US012465500B2

(12) United States Patent
Eggli et al.

(10) Patent No.: US 12,465,500 B2
(45) Date of Patent: Nov. 11, 2025

(54) BONE PLUG COMPRESSION INSTRUMENT

(71) Applicant: Stefan Eggli, Pierrafortscha (CH)

(72) Inventors: Stefan Eggli, Pierrafortscha (CH); Janosch Häberli, Bern (CH); Tom Overes, Langendorf (CH)

(73) Assignee: Stefan Eggli, Pierrafortscha (CH)

( * ) Notice: Subject to any disclaimer, the term of this patent is extended or adjusted under 35 U.S.C. 154(b) by 922 days.

(21) Appl. No.: 17/633,098

(22) PCT Filed: Jul. 24, 2020

(86) PCT No.: PCT/IB2020/057002
§ 371 (c)(1),
(2) Date: Feb. 4, 2022

(87) PCT Pub. No.: WO2021/024081
PCT Pub. Date: Feb. 11, 2021

(65) Prior Publication Data

US 2022/0331127 A1 Oct. 20, 2022

(30) Foreign Application Priority Data

Aug. 6, 2019 (CH) .................................... 00990/19

(51) Int. Cl.
*A61F 2/08* (2006.01)
*A61B 17/00* (2006.01)
(Continued)

(52) U.S. Cl.
CPC .... *A61F 2/4644* (2013.01); *A61F 2002/2839* (2013.01); *A61F 2002/4649* (2013.01); *A61F 2310/00359* (2013.01)

(58) Field of Classification Search
None
See application file for complete search history.

(56) References Cited

U.S. PATENT DOCUMENTS 5,329,846 A * 7/1994 Bonutti ..................... A61F 2/08 100/234
5,632,747 A * 5/1997 Scarborough ......... A61F 2/4644 606/86 R (Continued)

FOREIGN PATENT DOCUMENTS

CN 105997312 A * 10/2016 ........... A61F 2/4637
EP 2540239 A1 * 1/2013 ......... A61B 17/1767

(Continued)

OTHER PUBLICATIONS

JP Examination Report dated Apr. 9, 2024 as received in Application No. 2022-506420.

(Continued)

*Primary Examiner* — Ann Hu
(74) *Attorney, Agent, or Firm* — Maschoff Brennan

(57) ABSTRACT

A bone plug compression instrument that can be used to reshape includes a first compression element having a first cavity, a second compression element having a second cavity, and a base portion for supporting the first and second compression elements. The second compression element moves between first and second positions. In the first position, the bone plug compression instrument forms an open configuration, in which the first and second cavities are spaced apart from each other allowing the bone plug in a substantially non-compressed state to be inserted in a space between the first and second cavities In the second position, the bone plug compression instrument forms a closed configuration, in which the first and second cavities press against each other to form a combined cavity for compressing the bone plug received in the combined cavity. The combined cavity has at least a partially converging shape.

18 Claims, 10 Drawing Sheets

(51) Int. Cl.
*A61F 2/28* (2006.01)
*A61F 2/46* (2006.01)

(56) References Cited

U.S. PATENT DOCUMENTS

| | | | | |
|---|---|---|---|---|
| 6,432,142 | B1 * | 8/2002 | Kamiya | B30B 15/022 623/23.54 |
| 6,652,260 | B2 * | 11/2003 | Nelson | A61F 2/30942 425/436 RM |
| 8,322,253 | B2 * | 12/2012 | Howells | C21D 1/18 148/567 |
| 10,159,583 | B2 * | 12/2018 | Dietzel | A61F 2/4657 |
| 2001/0008979 | A1 * | 7/2001 | Bonutti | A61B 17/885 623/13.17 |
| 2009/0222052 | A1 | 9/2009 | Vandewalle | |
| 2017/0273795 | A1 * | 9/2017 | Neichel | A61F 2/4644 |

FOREIGN PATENT DOCUMENTS

| | | | | |
|---|---|---|---|---|
| ES | 2462490 | T3 * | 5/2014 | A61B 17/158 |
| WO | WO-9533415 | A1 * | 12/1995 | A61B 17/32053 |
| WO | WO-0149333 | A2 * | 7/2001 | A61F 2/4644 |
| WO | WO-0170136 | A2 * | 9/2001 | A61F 2/4455 |
| WO | 0150999 | A2 | 6/2002 | |
| WO | WO-2006090372 | A2 * | 8/2006 | A01N 1/142 |

OTHER PUBLICATIONS

AU Office Action dated Jan. 29, 2025 in application 2020325802.

CH Search Report in Application No. 00990/19 dated Oct. 30, 2019.

* cited by examiner

BONE PLUG COMPRESSION INSTRUMENT

TECHNICAL FIELD OF THE INVENTION

The present invention relates to a bone plug compression instrument for reshaping a bone plug from a first shape into a second shape. The invention also relates to a method of operating the compression instrument.

BACKGROUND OF THE INVENTION

In orthopaedic interventions around a knee, soft tissue grafts are often retrieved from a harvesting site and transferred to a target site. An example surgical intervention process for such a transplantation is the anterior cruciate ligament (ACL) reconstruction process, during which autologous tissues, such as tendons and ligaments, are used. One example technique for ACL reconstruction uses a quadriceps tendon and a patellar bone plug in the reconstruction process. This arthroscopically performed surgery includes the following procedures.

Procedure 1: Quadriceps Tendon Graft Harvesting

A central piece of the quadriceps tendon graft having a length of e.g. approximately 5 cm including an attached proximal patellar bone plug having a length of e.g. approximately 2 cm is harvested. This graft will serve as a replacement for the torn anterior cruciate ligament.

To harvest a bone plug from the patellar bone, most often a hollow drill is used. A hollow drill has a thin wall thickness and allows an intact bone plug to be drilled out, which is only minimally smaller than the hole or tunnel created by the drill. These bone plugs typically have an outer diameter of 8-12 mm and a length of 10-25 mm. Specifically when retrieving a patellar bone plug using a hollow drill, the plug is retrieved from the top side of the patella, flush with the outer face of the bone. After drilling for example to a depth of 20 mm, a chisel is used to cut off the bone plug at its far end.

Procedure 2: Tibial Tunnel Creation

A tunnel is drilled from the anterior and proximal tibia towards the natural tibial foot-print of the ACL. Preferably, a hollow drill is used in order to retrieve a bone plug, which can be placed back in the tibial tunnel, at a later step during the surgery. The tibial tunnel is shaped as a through bore having of a diameter of approximately 10 mm.

Procedure 3: Femoral Tunnel Preparation

A guide wire is placed through a femoral bone, defining the intended anatomical direction of a femoral tunnel. Using a cannulated drill, the guide wire is over-drilled and the tunnel is created. The femoral tunnel is shaped as a blind hole having a diameter of approximately 8 mm and a length of approximately 25 mm.

Procedure 4: Graft Placement/ACL Reconstruction

The patellar bone plug including the quadriceps tendon as retrieved in procedure 1 is impacted into the femoral tunnel. Most often, the tip of the cylindrical graft is given a conical tip, using cutting pliers. The conical tip, which extends over approximately one third of the bone plug length, facilitates the insertion of the bone plug into the femoral tunnel. Typically the reshaped tip has an outer circumference which is smaller than the entry circumference of the femoral tunnel.

In a next step, the quadriceps graft is pulled over the joint space, and fixated in the tibial tunnel. Most commonly, the tibial fixation may be carried out using a screw for suture attachment or an interference screw. A screw for suture attachment would be placed in the anterior side of the tibial bone, and suture is tied around the screw for fixation. Using an interference screw, a resorbable and thick screw is placed next to the ligament or tendon in the tibial tunnel, and it rigidly jams the tendon between the screw and the tunnel wall.

The success of the surgery greatly depends on the primary stability of the patellar bone plug in the femoral tunnel during the healing and osseointegration phase. This primary stability depends on the accuracy and reproducibility of the size and shape of the bone plug and the target hole. As described, currently the bone plug is reshaped manually, using pliers. This manual reshaping is not suitable for reproducibility and therefore the surgical outcome is less predictable. There is thus a need for an improved instrument for reshaping bone plugs.

SUMMARY OF THE INVENTION

It is an object of the present invention to overcome at least some of the problems associated with soft tissue graft fixation techniques, for instance in anterior cruciate ligament surgery. More specifically, an object of the present invention is to provide a medical instrument for preparation of a bone plug that allows the bone plug to be compressed and shaped in an accurate and reproducible manner.

According to a first aspect of the invention, there is provided a bone plug compression instrument as recited in claim 1.

The proposed novel bone plug compression instrument has the advantage that it can efficiently be used during a surgical intervention in which a bone plug is harvested and transferred to a target hole in a target bone. More specifically, the bone plug compression instrument allows a practitioner to intraoperatively resize and/or shape a bone plug in a controlled and reproducible manner. Therefore, the surgery becomes a standardised procedure providing reproducible and predictable results. Moreover, the surgery time can be reduced, and learning curves are reduced. The bone plug may be harvested using a hollow drill, circumferentially setting free the bone plug. As a result, the harvested bone plug typically has a cylindrical shape.

According to a second aspect of the invention, there is provided a kit comprising the bone plug compression instrument and a bone plug grafting instrument.

According to a third aspect of the invention, there is provided a method of operating the bone plug compression instrument.

Other aspects of the invention are recited in the detailed description and dependent claims attached hereto.

BRIEF DESCRIPTION OF THE DRAWINGS

Other features and advantages of the invention will become apparent from the following description of a non-limiting example embodiment, with reference to the appended drawings, in which.

DETAILED DESCRIPTION OF THE INVENTION

Figure 1:
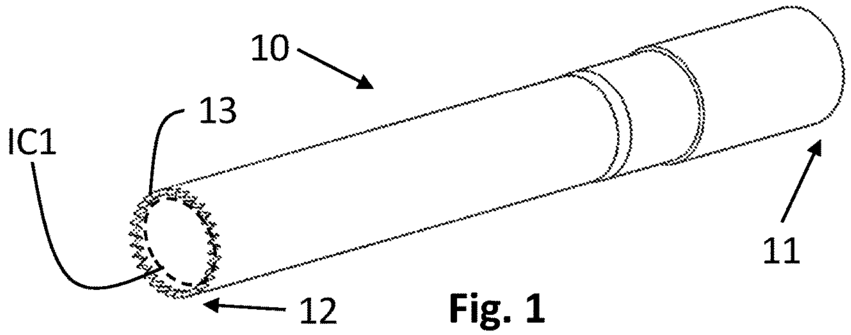
FIG. 1 illustrates in a perspective view an example bone plug grafting instrument.

An embodiment of the present invention will now be described in detail with reference to the attached figures. The embodiment is described in the context of a bone plug compression instrument configured to at least partially reshape a cylindrical bone plug by means of compression, but the teachings of the invention are not limited to this environment. The teachings of the present invention are equally applicable to differently shaped bone plugs as well. Identical or corresponding functional and structural elements which appear in the different drawings are assigned the same reference numerals.

Figure 2:
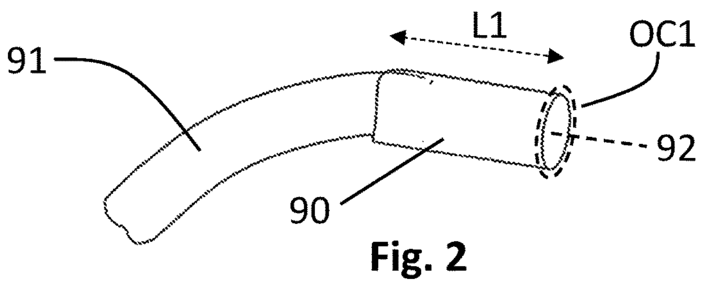
FIG. 2 illustrates in a perspective view an example bone plug together with an attached tendon.
Figure 3A:
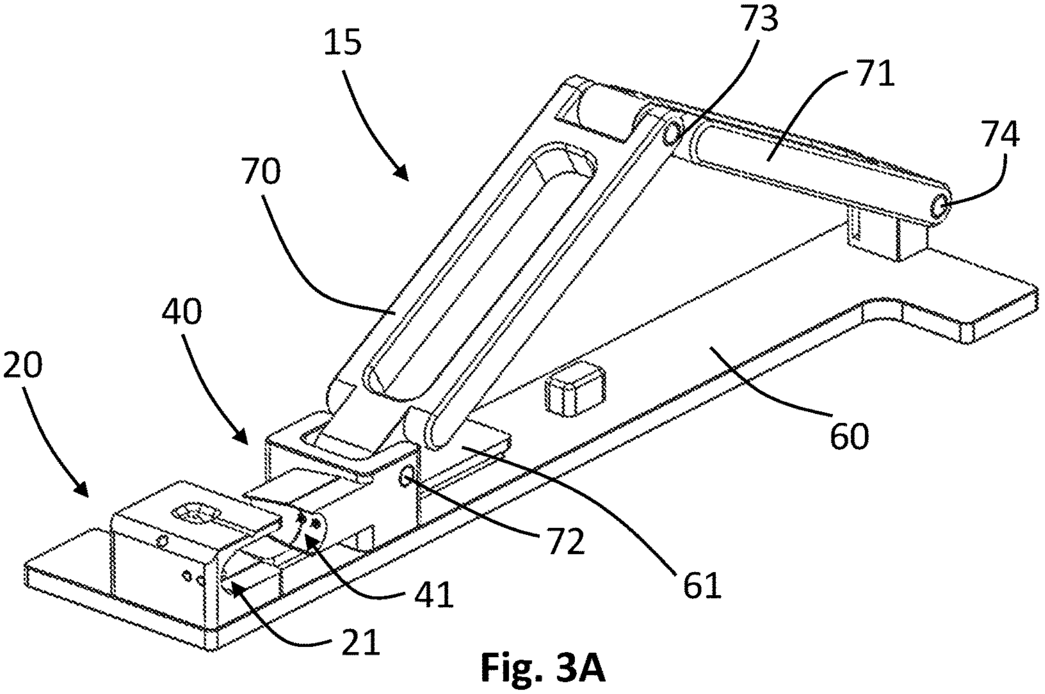
FIGS. 3A to 3G show in different views a bone plug compression instrument according to an example of the present invention.
Figure 3B:
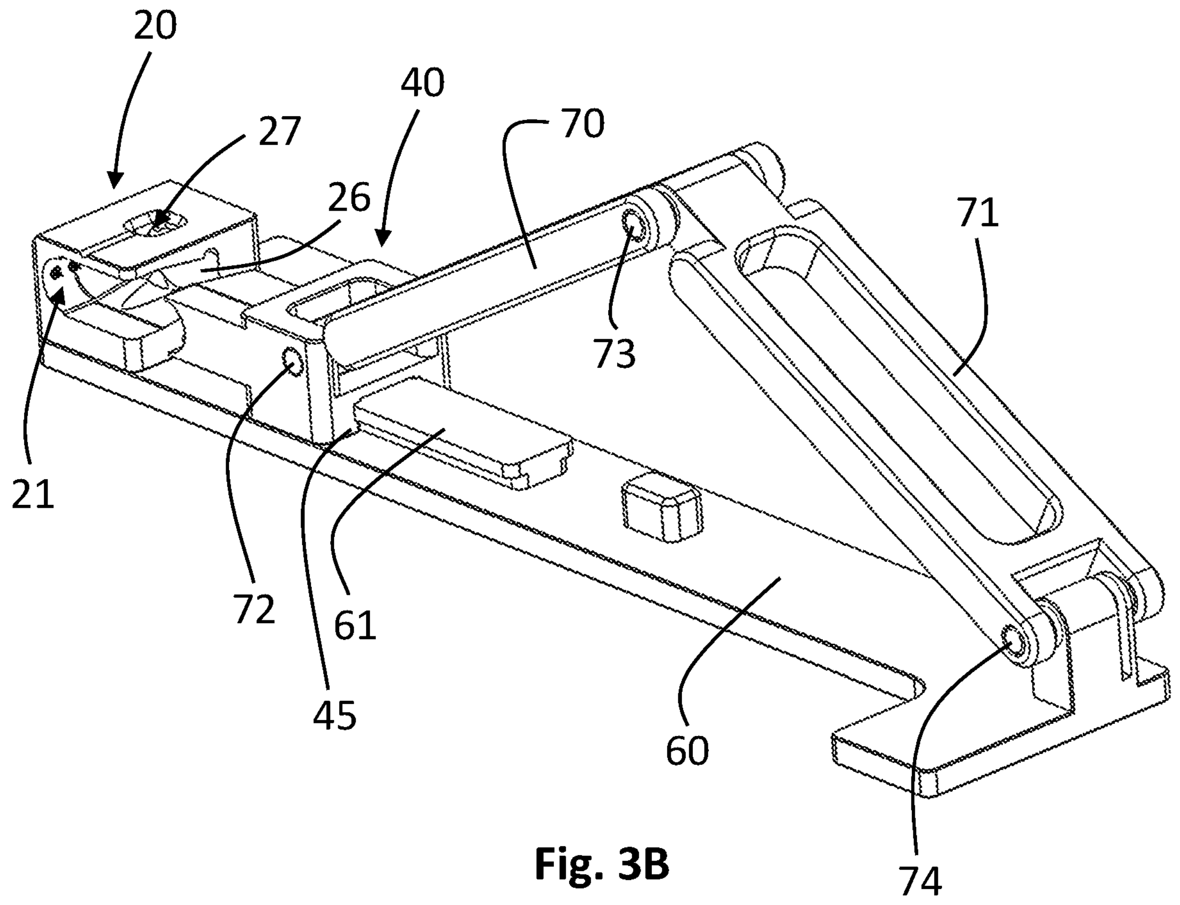
Figure 3C:
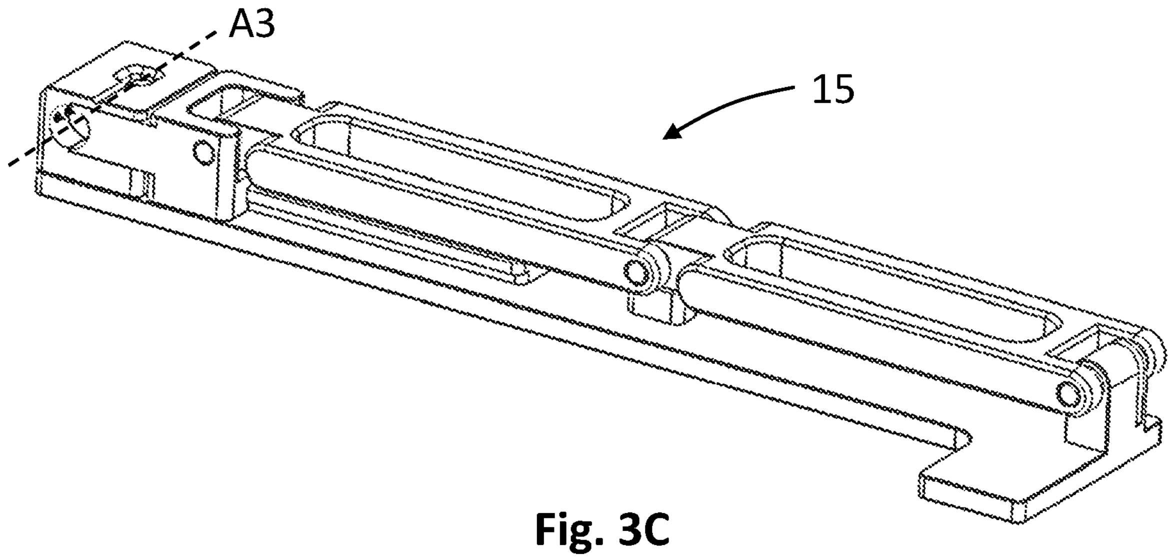
Figure 3D:
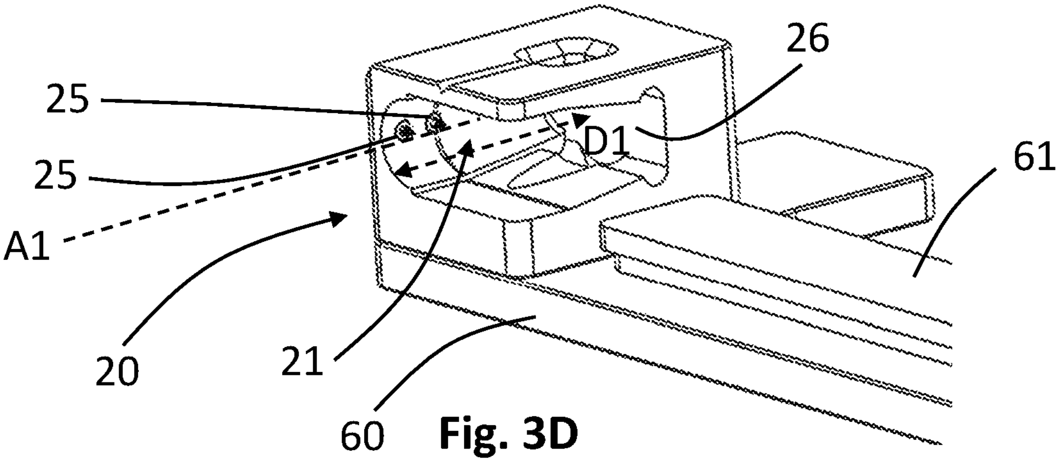
Figure 3E:
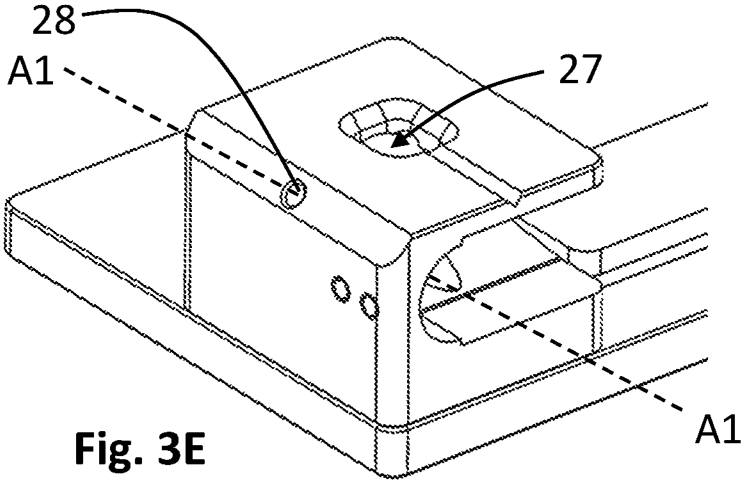
Figure 3F:
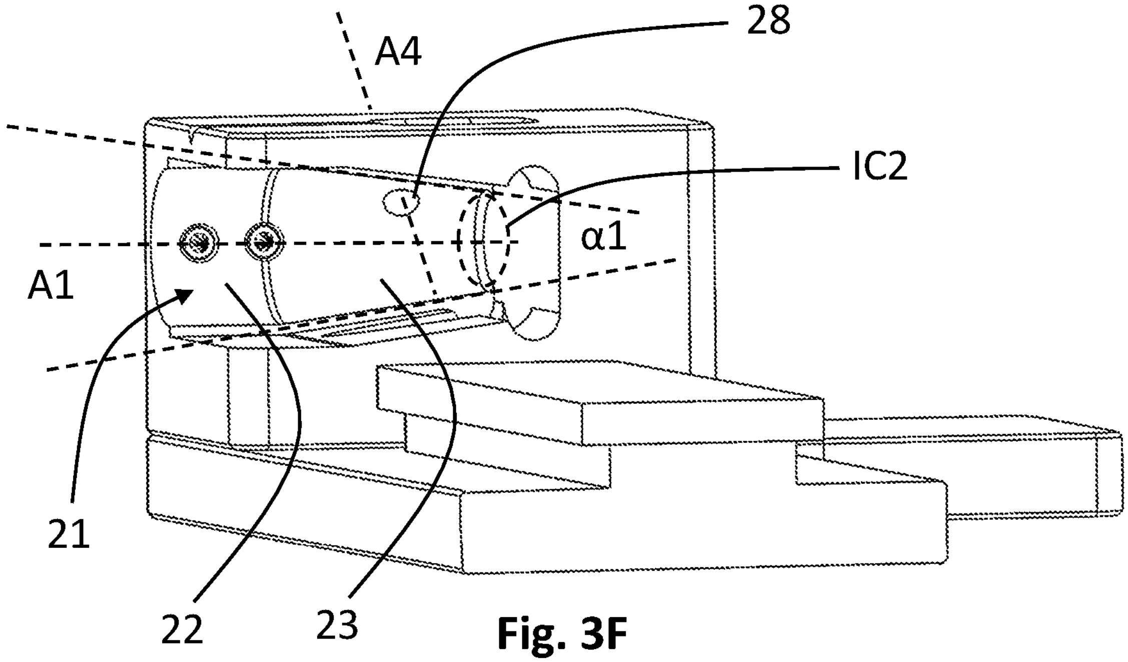
Figure 3G:
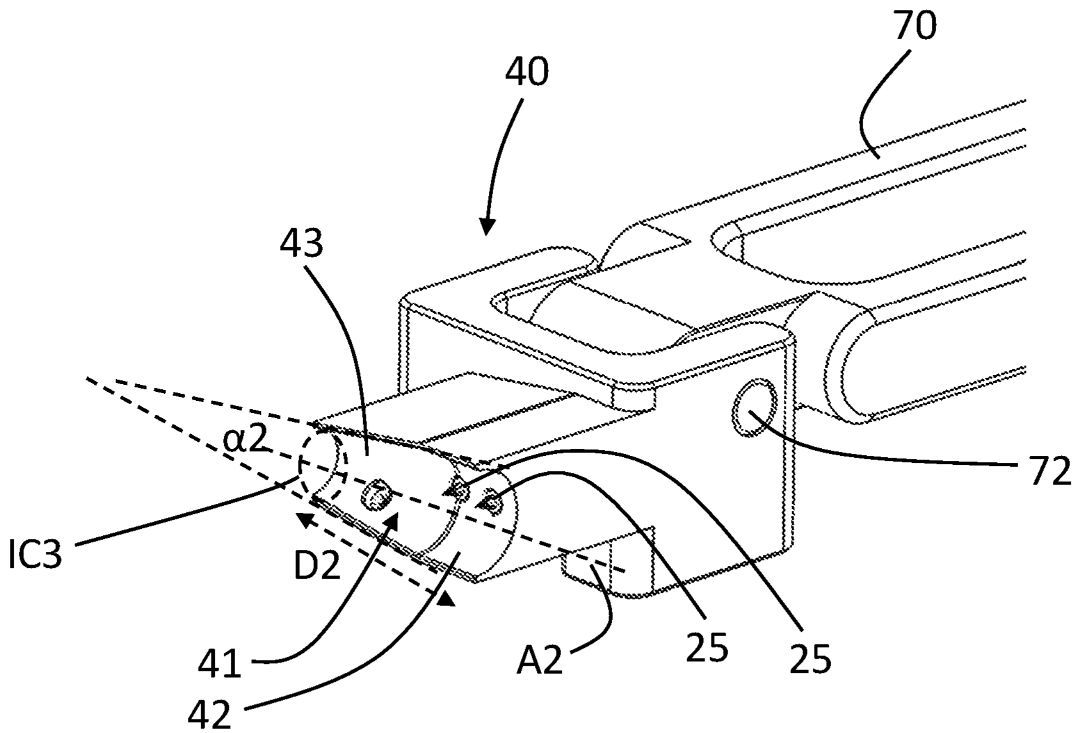

FIG. 1 shows an example grafting instrument 10 or a bone plug removal instrument, while FIG. 2 shows a bone plug 90 together with a tendon 91 attached to the bone plug. The grafting instrument 10 is sized and shaped as a thin-walled tube, i.e. a hollow tube thus comprising a bore or tunnel through it. It is to be noted that in the present description the word bore is understood to mean a tunnel but it does not necessarily imply any particular method of making the bore. A first end 11 of the grafting instrument is configured to be coupled to a surgical drilling machine, while a second, opposite end 12 comprises a cutting edge 13 or surface, in this example comprising cutting teeth. The tube-shaped grafting instrument 10 defines a first inner circumference IC1, which may or may not be substantially constant, and is intended to graft a bone plug of a first size with a first outer circumference OC1 and length L1. The bone plug 90 can be grafted using the grafting instrument 10. The length L1 may be between 10 mm and 25 mm, or more specifically between 18 mm to 22 mm, while the first outer circumference OC1 may be smaller than 38 mm, or smaller than 32 mm or more specifically between 25 mm and 38 mm. In this example, the bone plug is of a substantially cylindrical shape, and has a central or longitudinal axis 92. In this example, the first inner circumference IC1 and the first outer circumference OC1 are substantially equal. Hence, the inner and outer diameters of these objects are substantially equal. Thus, as shown in FIG. 1, the grafting instrument is a hollow drill element configured to be attached to a surgical drilling machine. By means of drilling, the grafting instrument 10 is advanced forward into the target bone. The bone plug to be removed is thus received in the bore, in this example in a form fit manner. The bone plug may be removed out of the target bone together with the grafting instrument or separately. Specifically, when retrieving a patellar bone plug using a hollow drill, the plug is retrieved from the top side of the patella, flush with the outer face of the bone. After drilling for example to a depth of 20 mm, a chisel is used to cut off the bone plug at its far end. The bone plug is located within the grafting instrument. Alternatively, the grafting instrument can be configured, i.e. shaped, as a punching instrument, which is advanced into the target bone by hammering. In this case, the bone plug can be separated from the rest of the target bone by turning the grafting instrument to break off the bone plug, which turns together with the grafting instrument. It is to be noted that by a bone grafting instrument may be understood any kind of bone plug removal apparatus or instrument. In other words, the bone grafting instrument may be used alone or in combination with another tool to remove the bone plug from the target bone.

FIGS. 3A to 3G show an example of the bone plug compression instrument 15 in different views. The compression instrument as shown in FIGS. 3A to 3G functions according to a toggle clamp mechanism, and comprises: a base or support element or portion 60 with an integrated first compression mould or tool element or portion 20 (also simply referred to as a first compression element), a second compression mould or tool element or portion 40 (also simply referred to as a second compression element), a first lever arm or lever 70, a second lever arm or lever 71, a first connection mechanism, which in this example is a first hinge mechanism (or simply a first hinge) 72, a second connection mechanism, which in this example is a second hinge mechanism (or simply a second hinge) 73, and a third connection mechanism, which in this example is a third hinge mechanism (or simply a third hinge) 74 pivotally connecting the first and second levers to the base element 60. The first, second and third hinge mechanisms 72, 73, 74 define a first pivot axis, a second pivot axis and a third pivot axis, respectively, which in this example are substantially parallel to each other, and orthogonal to the longitudinal axis of the base element 60. The first compression mould element 20 is in this example fixed to the base element and is not able to move with respect to the base element 60. The second compression mould element 40 is linked by the first hinge mechanism 72 to the first lever 70 to be moved or displaced according to a defined path between a first position and a second, different position. In the first position, the bone plug compression instrument 15 is in an open, parted or separated configuration or state, while in the second position, the bone plug compression instrument 15 is in a closed configuration or state as explained later in more detail. The closed configuration can be reached from the open configuration by pressing (in this example downwards) any one of the first and second levers 70 and 71.

The advantage of the toggle clamp mechanism, is that it works according to the knee lever principle and can be operated with little expenditure of force. Furthermore, locking or self-restriction is guaranteed if the dead centre position (alignment of the three hinges or points of the joint) is exceeded. Very high clamping forces can be achieved with toggle clamps. In theory, at the moment of alignment of the first and second levers, an infinite compression force is present.

The first compression mould element 20 comprises a first compression or mould cavity 21 defining a first central or longitudinal axis A1 (first cavity central axis). The first mould cavity 21 is in this example sized and shaped as a partially tapered cavity, including a first constant diameter cavity portion 22 and a first converging or tapering cavity portion 23 with a tapering angle $\alpha 1$ with its smallest circumference (or more precisely its smallest virtual circumference as the first mould cavity does not extend over the full 360° rotation) referred to as a second inner circumference IC2. In the present example, when a shape is said to converge or partially converge, then it is understood that the shape outline(s) or its/their virtual extension(s) (or side profile outlines or their virtual extensions) converge. In the present example, the converging cavity portion 23 starts converging in the middle third portion of the first mould cavity 21. Alternatively, the converging portion can start at any position along the first cavity depth or length D1 or can extend over the full cavity depth D1. In the present description, by a converging cavity or surface is meant that a first cavity end has a smaller circumference length compared to a second, opposite cavity end. The converging effect may take place by a tapering effect along a straight curve, but it may instead take place along a curved or irregular curve, or along any combinations of them. The converging effect provides a reduction of the average circumference. The converging effect can also be created by an incrementally stepped shape of the cavity.

Similarly to the first compression mould element 20, also the second compression mould element 40 comprises a second compression or mould cavity 41 defining a second central or longitudinal axis A2 (second cavity central axis). In the present example, the shape and size of the second mould cavity is complementary or is a mirror image to the shape and size of the first mould cavity. In other words, the second mould cavity 41 is sized and shaped as a stepped cavity, including a second constant diameter cavity portion 42 and a second converging or tapering cavity portion 43 with a tapering angle $\alpha$2 with its smallest circumference (or more precisely its smallest virtual circumference as the second mould cavity does not extend over the full 360° rotation) referred to as a third inner circumference IC3. In the present example, the converging cavity portion 43 starts converging in the middle third of the second mould cavity 41. Alternatively, the converging portion can start at any position along the second cavity depth or length D2, or can extend over the full cavity depth D2. In the present example, the first cavity depth D1 substantially equals the second cavity depth D2. The first and second compression mould cavities may extend at least 120° relative to their respective central or rotation axis A1, A2 or more specifically between 160° and 200°.

As a result of the compression step as will be explained later, and thanks to the converging cavity shapes, any compressed bone plug end has a smaller circumference length compared with the opposite end. To allow compressing the bone plug, at least one of the second and third inner circumferences IC2 and IC3 is smaller than the first inner circumference IC1 of the grafting instrument, and/or the first outer diameter OC1 of the bone plug. It is to be noted that in the present description the word circumference is used to describe the enclosing boundary (or its length) of a curved geometric figure or object. More specifically, the word outer circumference may be used to describe the circular enclosing boundary of a cylinder, while the inner circumference may be used to describe the inner boundary of a tube. Although in the present example, the uncompressed bone plug is of a cylindrical shape, the word circumference is not limited to a circular boundary, but also defines a general distance around an object, such as a perimeter, border, boundary, periphery, etc. For instance, according to an example, the word circumference may describe the boundary of an oval-shaped element or cavity. Other shapes such as polygons, or irregular shapes also have an (average) external or internal boundary forming a circumference.

In the present example, at least one of the mould cavities 21, 41 comprises at least one spike 25 for fixation of the bone plug. In this example, the spikes are oriented substantially orthogonally with respect to the first and second cavity axes A1, A2. The purpose of the spike(s) is to penetrate the bone plug during the transition from the first configuration into the second configuration as depicted later. During this transition, both mould cavities are configured to compress the bone plug from the opposite sides. As a reaction to the compression forces, and to the creation of the converging tip on the bone plug, the bone plug may tend to translate out of the mould cavities. The spikes are designed to inhibit this unwanted movement.

In the first configuration, the first and second mould cavities 21, 41 are spaced apart to receive the bone plug of the first size and/or shape. This means that the open or separated cavities provide enough clearance for placement of the bone plug within or between the cavities. As can be seen in the figures, at least one of the compression mould elements 20, 40 (in this example the first compression mould element) has an enlarged space next to the respective mould cavity so that the bone plug of the first size can fit in this space before its compression. In the second configuration, the combined cavity volume of the first and second mould cavities 21, 41 is smaller than the volume of the uncompressed bone plug. This enables reshaping and resizing the bone plug while it is being compressed. In the second configuration, the first and second mould cavities form a combined mould cavity defining a third central axis A3 or combined cavity central axis, which in this example coincides with the first or second cavities axes (in the second configuration). In the present example, the relative movement of the mould cavities 21, 41 is a linear motion (i.e. a translational motion) along a straight path. To facilitate this motion, the base element 60 and the second compression mould element 40 comprise a first guide element 61 and a second guide element 45, respectively, which have complementary shapes and are configured to engage with each other. More specifically, the base element 60 in this example comprises a rail 61 arranged to engage an engaging element (having a complementary shape to the shape of the rail) on the second compression mould element to allow the engaging element to slide along the rail. In the present example, only one translational degree of freedom is present. Alternatively, the second guide element 45 would form the rail, and the first guide element would have a complementary shape to the shape of the rail.

Alternatively or in addition, the first and second compression mould elements may be connected with a hinge, providing a connection means allowing the combined cavity to be opened and/or closed.

To provide accuracy of placement, at least one of the first and second mould cavities 21, 41 includes a back wall 26, functioning as a depth reference for correctly positioning the uncompressed bone plug. An opening or window 27 functions as an extra aid during the placement step, as depicted later with reference to FIGS. 4A to 4K. Furthermore, at least one of the compression mould elements (in this example the first compression mould element 20) has a drilling channel or tunnel 28 having a central axis A4, sized and shaped to receive a drill bit 130 (see FIG. 4G), where the drilling channel extends into at least one mould cavity and is directed towards the central axis A3 of the combined mould cavity in the closed configuration. In this example, the axes A3 and A4 intersect or substantially intersect. The drilling channel is used to drill a hole centrally through the bone plug. The hole is intended for a suture to be looped through the created hole. The drilling channel may have a diameter between 1.5 mm and 3.5 mm, or more specifically between 1.8 mm and 2.5 mm. The centre of the drilling channel is spaced from the back wall 26 at a distance between 3 mm and 11 mm, or more specifically between 7 mm and 9 mm.

Figure 4A:
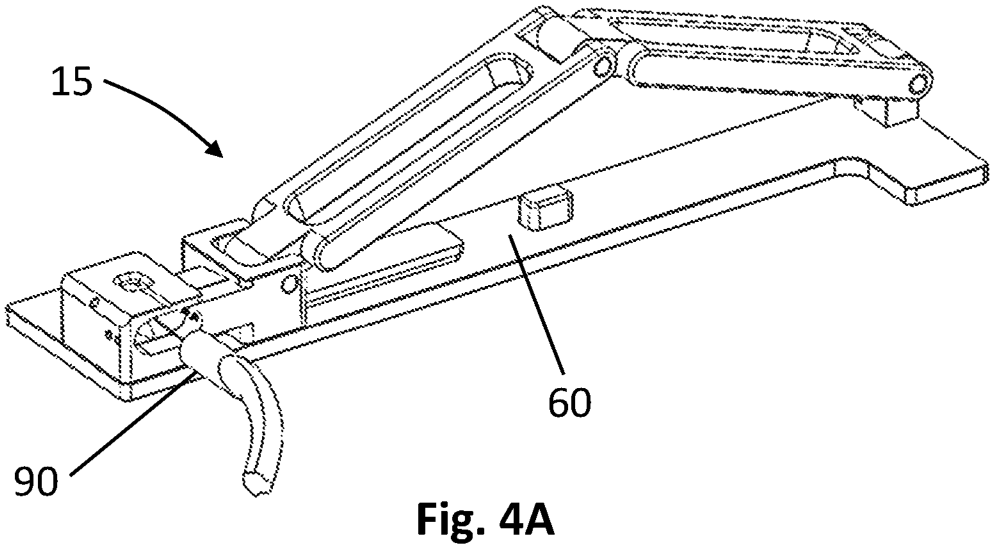
FIG. 4A to 4K depict in different perspective views the steps of a method of operating the bone plug compression instrument of FIGS. 3A to 3G for resizing and/or reshaping the bone plug.
Figure 4B:
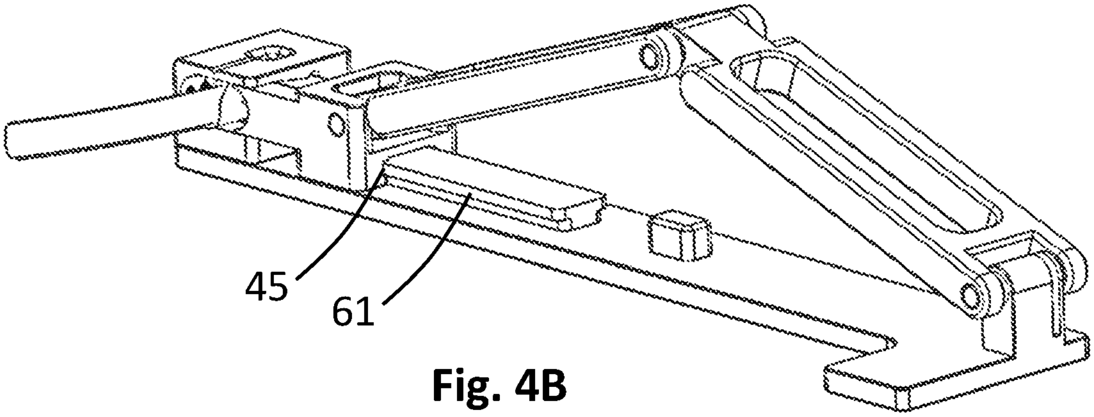
Figure 4C:
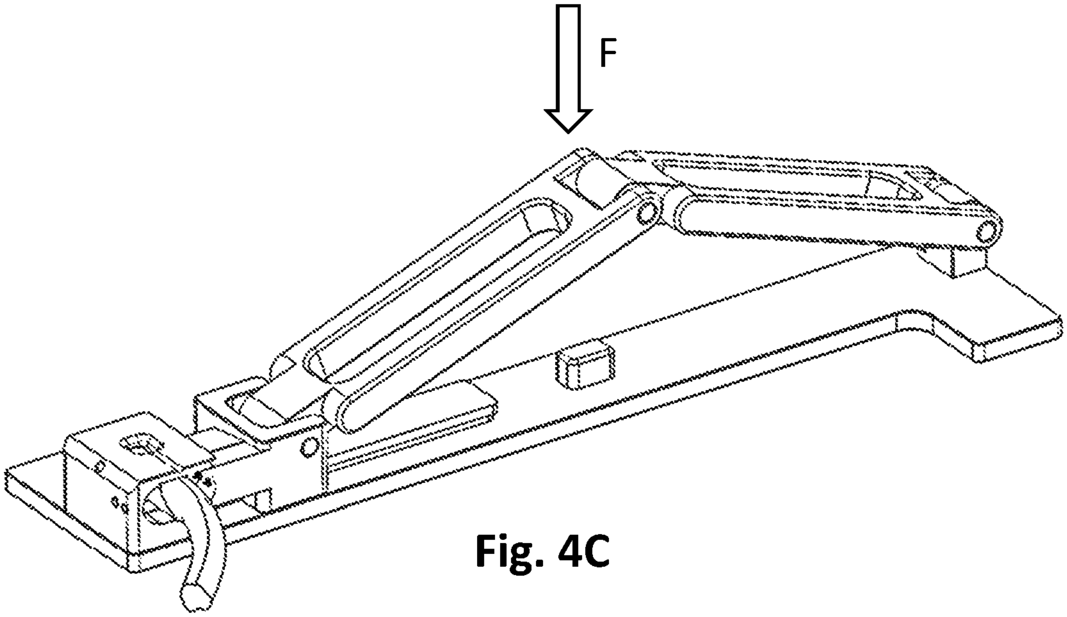
Figure 4D:
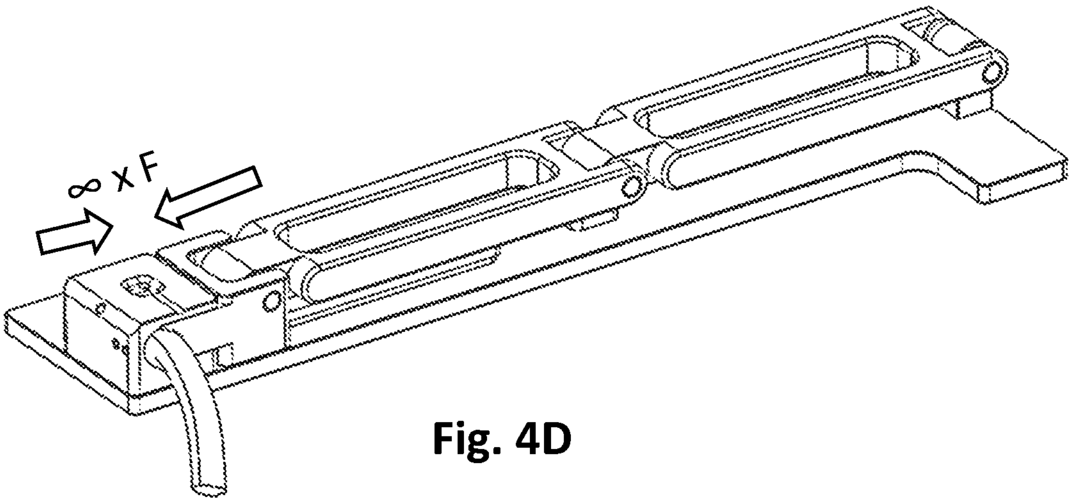
Figure 4E:
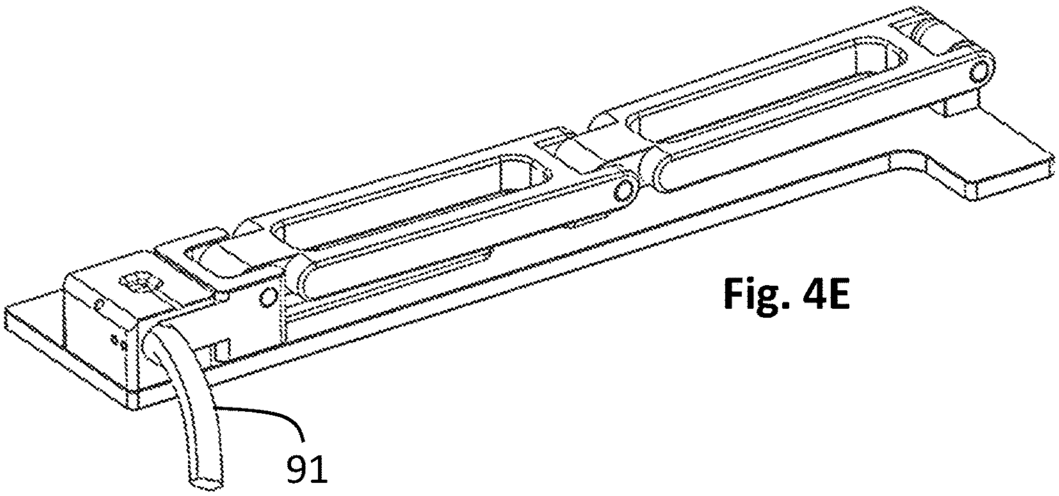
Figure 4F:
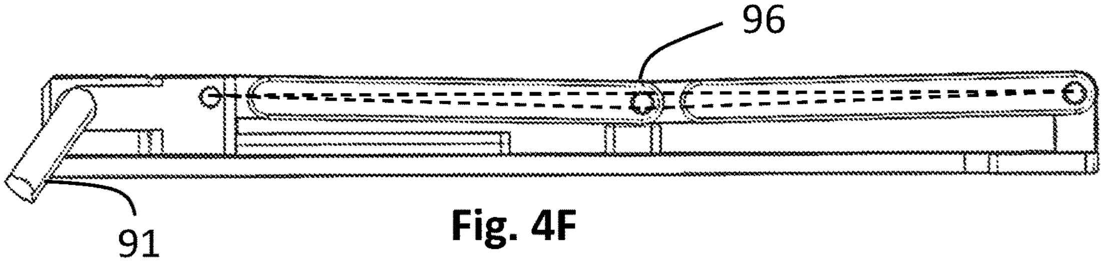
Figure 4G:
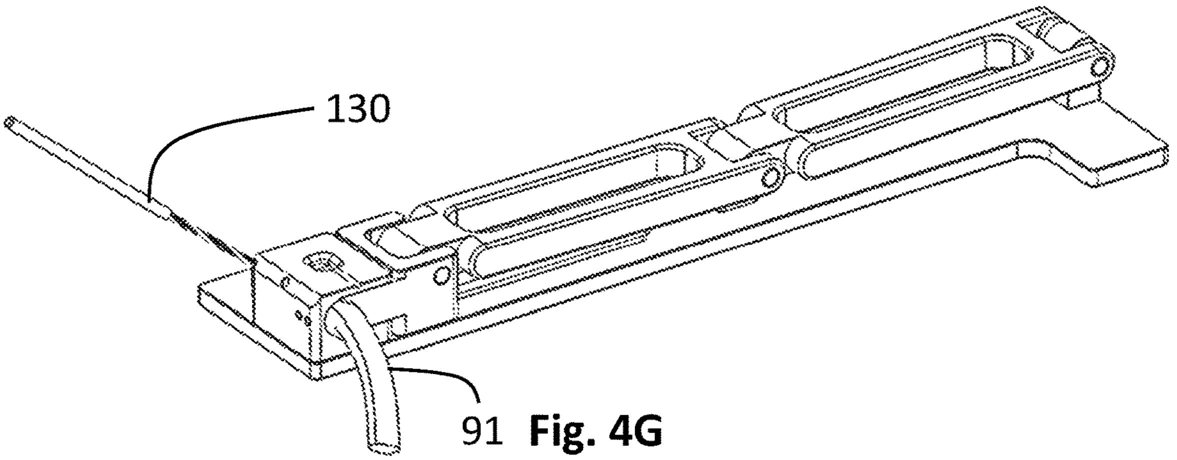
Figure 4H:
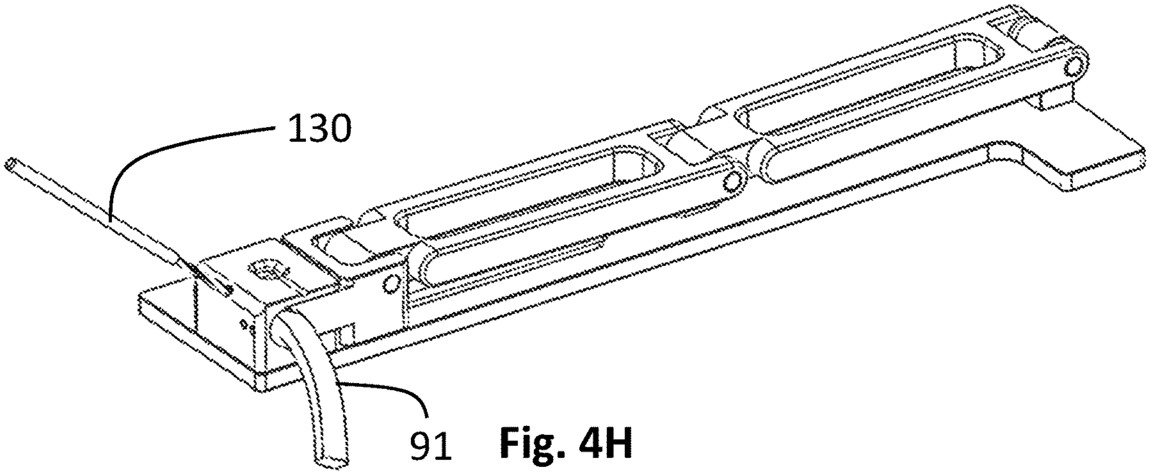
Figure 4I:
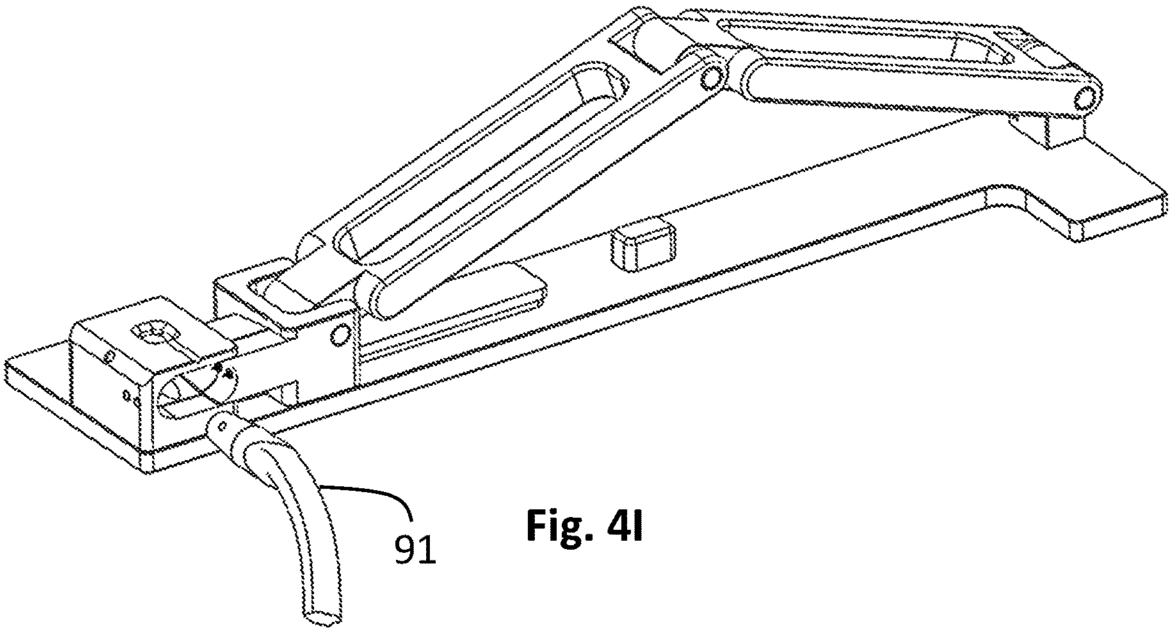
Figure 4J:
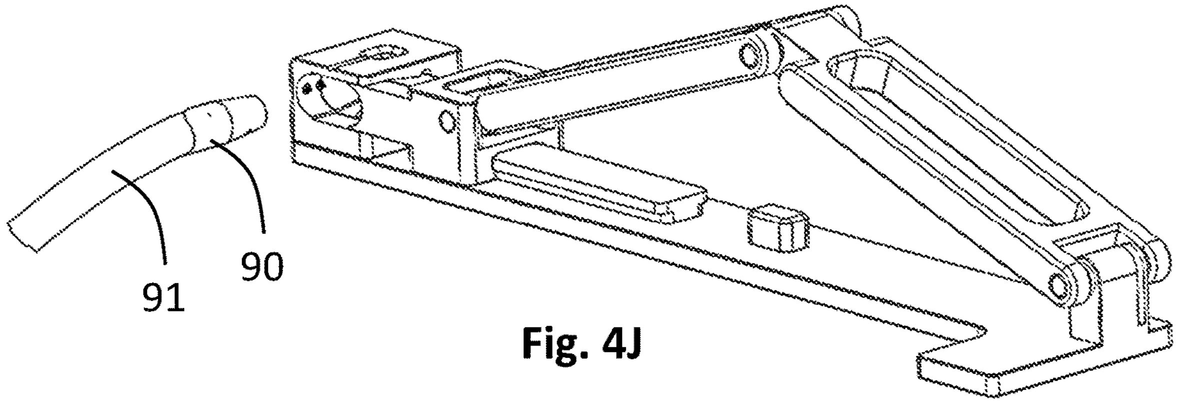
Figure 4K:
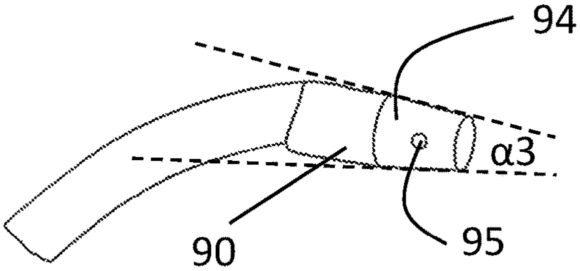

FIGS. 4A to 4K illustrate the steps of operating the bone plug compression instrument 15 to reshape the bone plug 90. FIG. 4A depicts the compression instrument in the first configuration. The cylindrical bone plug is shown in front of the instrument. FIGS. 4B and 4C depict the situation, in which the bone plug 90 is being inserted into the compression instrument between the first and second mould cavities 21, 41. The bone plug is inserted in the space between the cavities until it reaches the back wall 26 of the first mould cavity 21. FIG. 4D shows the compression instrument 15 in the second and closed configuration. Due to the toggle clamp mechanism according to the knee-lever principle, a theoretically infinite compression force is exerted on the bone plug as soon as the dead centre position is reached. The dead centre position is the position wherein the central axes of all the hinges of the combined cavity closing/opening mechanism (one axis per hinge) are located in one single plane. FIGS. 4E and 4F show the compression instrument in an overstretched or locked configuration. By exceeding the dead centre position 96, self-restriction or locking is achieved. FIGS. 4G and 4H show the drilling of the hole through the bone plug. The drilling channel 28 guides or directs the drill bit towards the centre of the bone plug 90. FIGS. 41 and 4J show the removal of the reshaped bone plug having a second size and/or shape out of the bone plug compression instrument 15. FIG. 4K shows the reshaped bone plug including a tapered end 94 with a tapering angle α3 and the suture hole 95. Thus, in this example, the bone plug has at least a partially conical shape. It is to be noted that the tapering angles α1, α2, α3 may be between 1° and 70° or more specifically between 5° and 60° or between 10° and 20°.

Figure 5A:
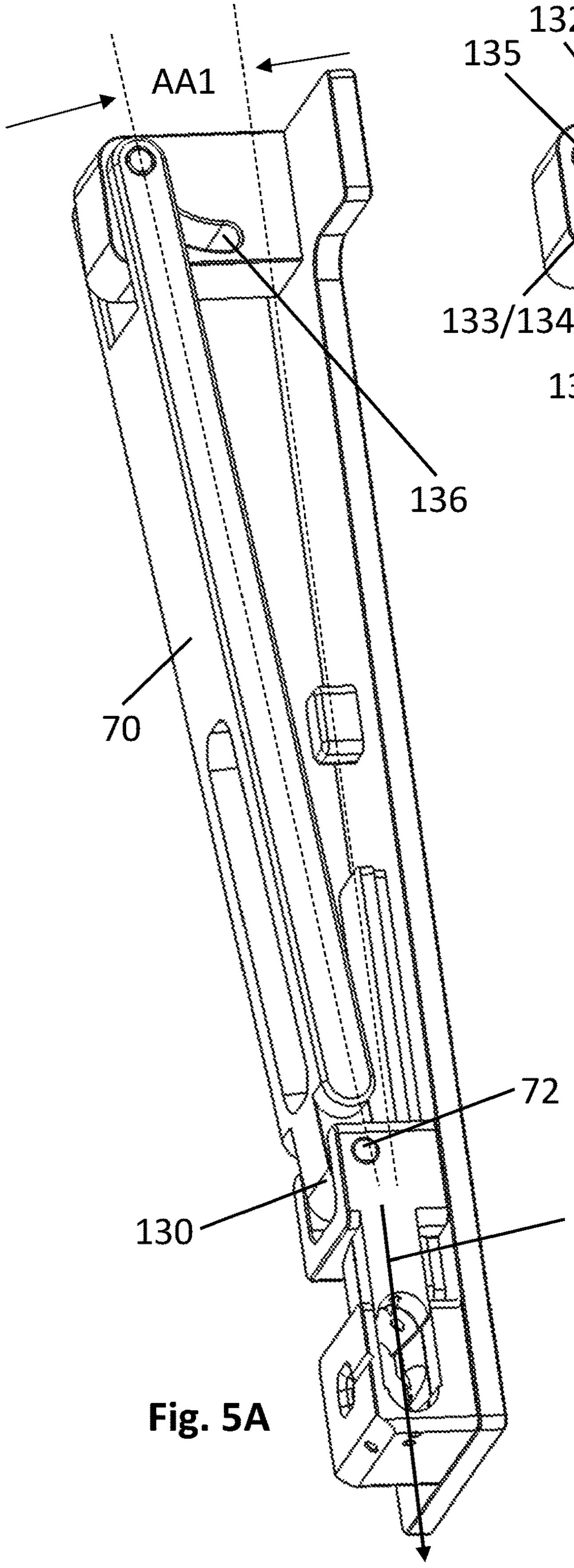
FIGS. 5A and 5B show an alternative design of the bone plug compression instrument comprising a guiding slot.
Figure 5B:
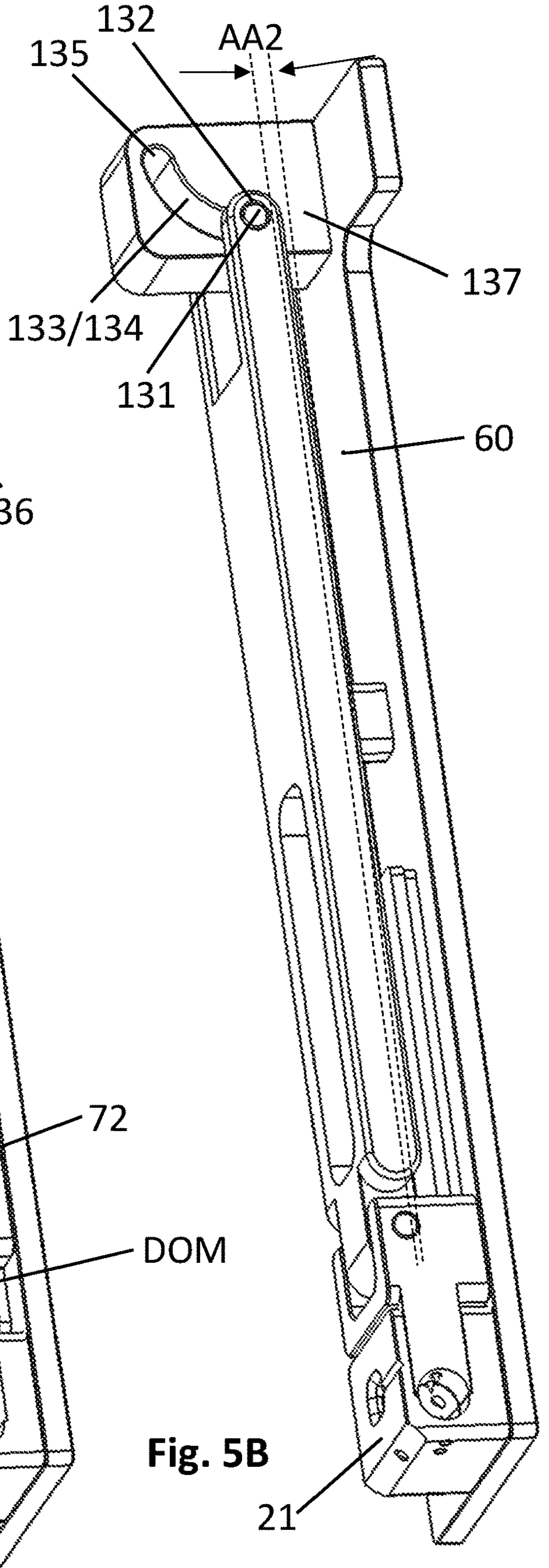

FIGS. 5A and 5B show an alternative design of the bone plug compression instrument, where the instrument comprises a long first lever 70 having a first end 130 and a second, opposite end 131, and a length 'L'. FIGS. 5A and 5B depict the bone compression instrument in an open and closed configuration or state, respectively. The first lever is coupled, in this example rotatably coupled, to the second mould cavity 41 by means of a first connection mechanism 72 at the first end 130. In this example, the first connection mechanism 72 is a hinge. The second end 131 is engaged against a guiding face, path, or surface 133 arranged on the base 60, mating with an instant contact area or surface 132. The contact surface is in this example part of an engagement element, which in this case is a pin. The contact surface 132 is thus arranged in a guiding slot at least partially delimited by the guiding surface 133. The combination of the path and the second end 131 forms an instant centre of rotation ICOR. During operation of the clamp, the instant contact surface travels along the guiding path 133. In this example, the guiding path is a seat face 134 arranged on a projection 137 or a protruding element 137 extending upwards from the base. The seat face 134 is directed towards the first and second moulds. Furthermore, the guiding path comprises a path start 135 and a path end 136.

In this example, the first and second moulds 21, 41 are engaged in a sliding manner having a direction of movement DOM. FIG. 5A shows the bone compression instrument in an open configuration. In this open configuration, the first lever is oriented at a first acute angle AA1 to the direction of movement DOM. FIG. 5B shows the bone compression instrument in a closed configuration. In this closed configuration, the first lever is oriented at a second acute angle AA2 to the direction of movement DOM, where AA2 is smaller than AA1. Furthermore, in the present example, the instant contact surface 132 is located closer to the first mould in the closed configuration than in the open configuration. Preferably the second acute angle is close to zero or substantially zero in order to apply maximal compression forces on the bone plug. In the present example, the guiding path is curved, but alternatively the guiding path may be straight (which may extend orthogonally or substantially orthogonally to the DOM, or straight and angled with respect to the DOM.

Figure 6:
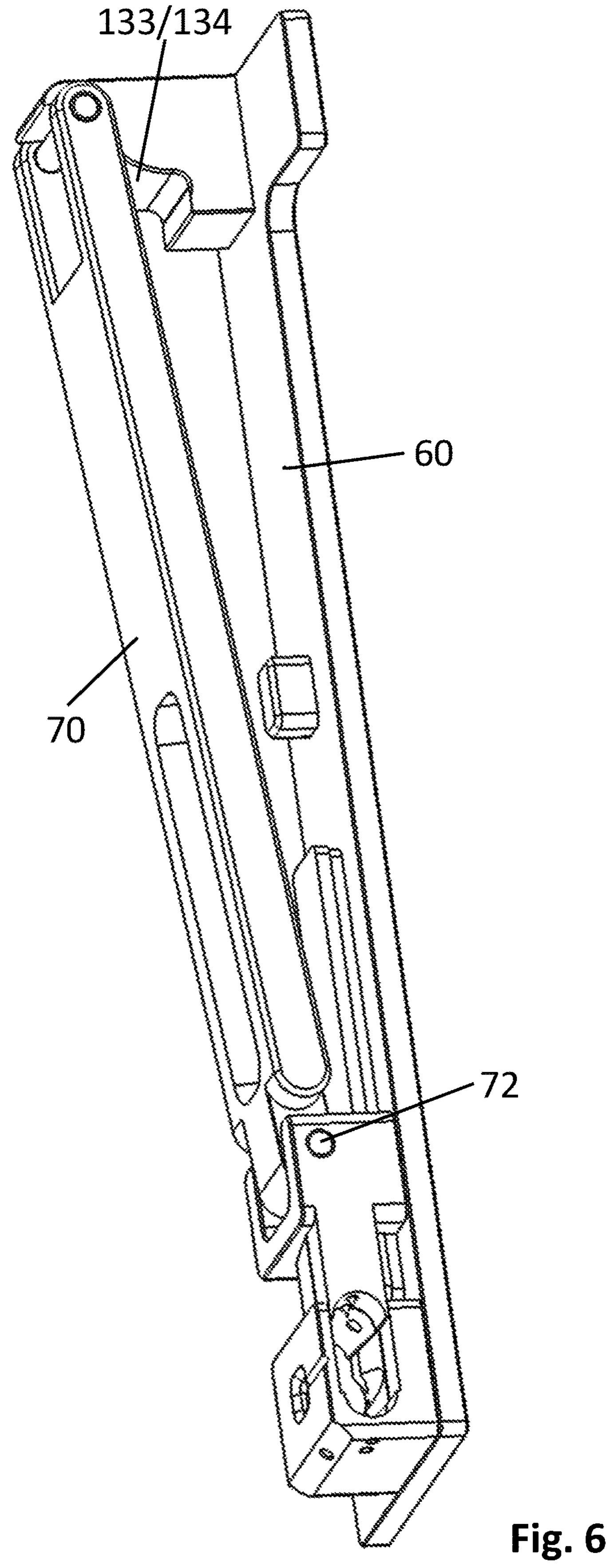
FIG. 6 shows yet another design of the bone plug compression instrument comprising an open guiding seat.

FIG. 6 shows yet another variant of the bone compression instrument. This variant is very similar to the variant of FIGS. 5A and 5B, but with the difference that the engagement element with the contact surface is not arranged in a slot, but glides on the seat 134, which is not part of a slot.

Figure 7:
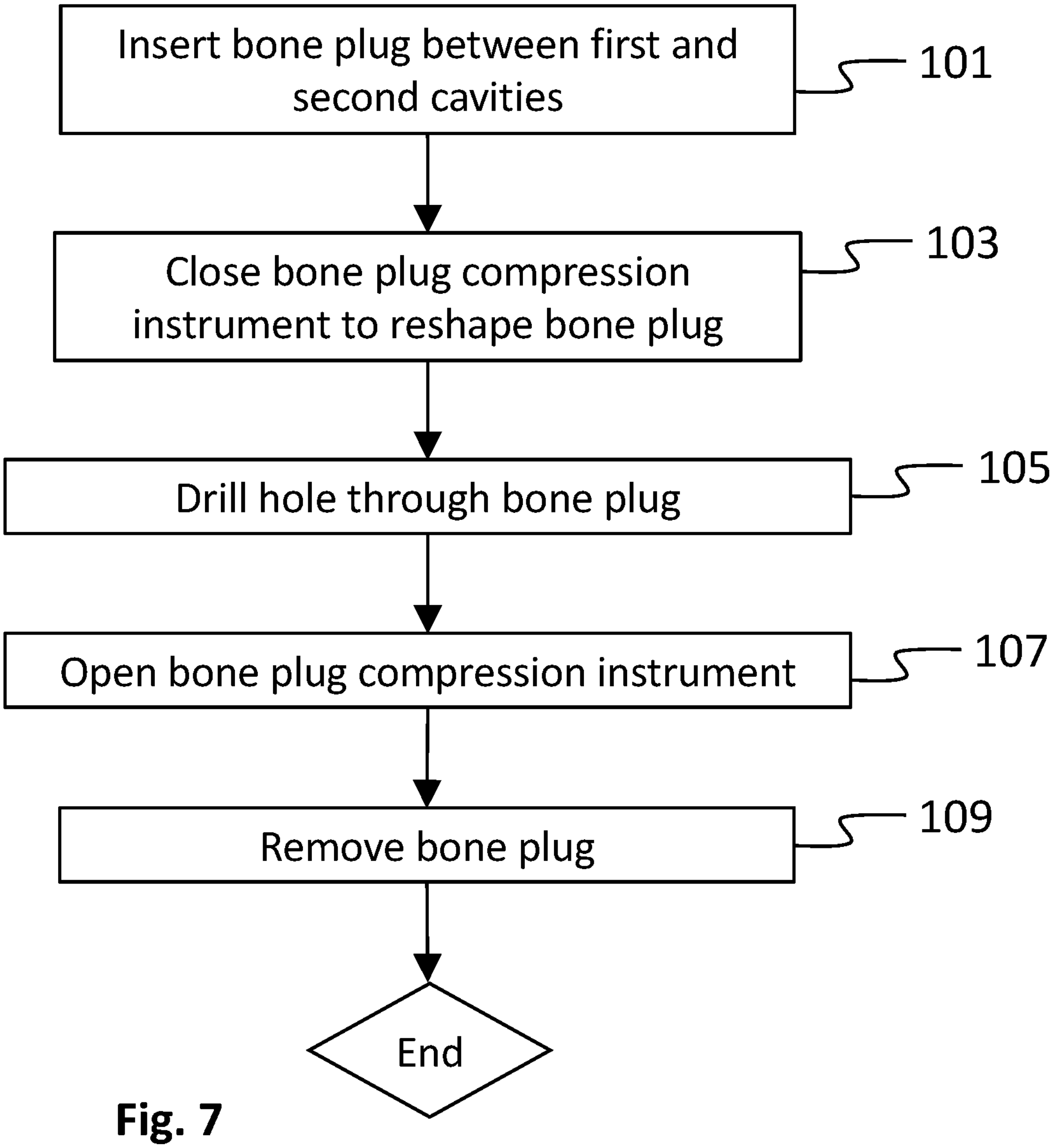
FIG. 7 shows a flow chart summarising the method of operating the bone plug compression instrument.

The flow chart of FIG. 7 summarises the steps of operating the bone plug compression instrument 15. In step 101, the bone plug 90 is inserted in the space between the first and second mould cavities 21, 41 while the instrument is in the open configuration. In this configuration, the first and second levers 70, 71 are elevated with respect to the base element 60 of the instrument. In step 103, the bone plug compression instrument is closed by pressing down at least one of the levers so that the first and second levers reach an opposite, non-elevated state, in which they are substantially parallel to the base portion or have exceeded the dead centre position. By closing the bone plug compression instrument, the bone plug is simultaneously reshaped so that the bone plug obtains the shape of the combined cavity. In step 105, a hole is drilled through the bone plug, optionally substantially orthogonally to the central or longitudinal axis 92 of the bone plug. In step 107, the bone plug compression instrument 15 is opened by lifting the first and second levers. This causes the second mould cavity 40 to glide along the rail 61. In step 109, the reshaped and resized bone plug is removed out of the bone plug compression instrument.

The compression instrument according to the present embodiment is designed as a table-top instrument. This means that the instrument can be statically placed on an instrumenting table. For this reason, the instrument includes the large and stable base element 60. Alternatively, the bone plug compression instrument 60 may be a hand-held instrument, shaped for example as a pair of pliers.

As depicted above, the compression instrument includes the first and a second mould cavities 21, 41, which have a smooth inner surface. Alternatively, the inner surface of at least one of the cavities may include a rough structure and/or axial, concentric or oblique ribs, etc. to improve friction between the bone plug and the cavity surfaces. i.e. the compression surfaces.

To summarise, it was described above a bone plug compression instrument 15 for reshaping a bone plug 90. The bone plug compression instrument 15 in one example comprises: a first compression element 20 comprising a first cavity 21; a second compression element 40 comprising a second cavity 41; and a base portion 60 for supporting the first compression element 20 and the second compression element 40. At least one of the first compression element 20 and the second compression element 40 is configured to move relative to the other compression element 20, 40 or relative to each other between a first position and a second, different position of the respective compression element(s) 20, 40. In the first position the bone plug compression instrument 15 forms an open configuration, in which the first and second cavities 21, 41 are spaced apart from each other allowing the bone plug 90 in a substantially uncompressed state to be inserted in a space between the first and second cavities 21 or their respective compression surfaces, 41, and in the second position the bone plug compression instrument 15 forms a closed configuration, in which the first and second cavities 21, 41, or the first and second compression elements, are configured to be pressed against or towards each other to form a third, combined cavity for compressing the bone plug received in the combined cavity. The combined cavity has at least partially tapered or converging/convergent shape. The combined cavity has a compression surface configured to be in direct or intimate contact with a bone plug, the compression surface extending over at least 300° or 340°, preferably substantially 360° in relation to its combined cavity central axis A3.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims. For example, it is possible to arrange the compression instrument so that both the first and second compression elements could move with respect to each other. Further embodiments may be obtained by combining the teachings of at least two design variants.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A bone plug compression instrument for reshaping a bone plug, the bone plug compression instrument comprising:

a first compression element comprising a first cavity comprising a first compression surface;

a second compression element comprising a second cavity comprising a second compression surface; and a base portion for supporting the first compression element and the second compression element, wherein:

the second compression element is configured to move relative to the first compression element between a first position and a second, different position, in the first position, the bone plug compression instrument forms an open configuration, in which the first and second cavities are spaced apart from each other allowing the bone plug in a substantially uncompressed state to be inserted in a space between the first and second compression surfaces, and in the second position, the bone plug compression instrument forms a closed configuration, in which the first and second cavities form a combined cavity for compressing the bone plug received in the combined cavity, and wherein the combined cavity has at least a partially converging shape, wherein the base portion comprises a first guide element, and the second compression element comprises a second guide element configured to engage with the first guide element such that the second compression element is configured to slidingly engage the first guide element such that a sliding movement of the second compression element with respect to the first guide element enables the second compression element to move at least from the first position to the second position, and wherein the bone plug compression instrument comprises a first lever arm pivotably connected to the second compression element by a first connection mechanism such that when the first lever arm is in an elevated position with respect to the base portion, the bone plug compression instrument is in the open configuration, and when the first lever arm is in an opposite, non-elevated position with respect to the base portion, the bone plug compression instrument is in the closed configuration.

2. The bone plug compression instrument according to claim 1, wherein:

the combined cavity is of a substantially rotationally symmetrical shape, and at least one of the first cavity and the second cavity extends over at least 120° in relation to its respective cavity central axis.

3. The bone plug compression instrument according to claim 1, wherein the first and second cavities have a tapered shape such that the first and second cavities are tapered along their substantially entire length or along a portion of their length only.

4. The bone plug compression instrument according to claim 1, wherein:

the first and second cavities have complementary shapes to form the combined cavity in the closed configuration, and the combined cavity has a compression surface extending over at least 340° in relation to its combined cavity central axis.

5. The bone plug compression instrument according to claim 1, wherein:

the first guide element is a rail, the second guide element has a complementary shape to the shape of the rail, or the second guide element is a rail, and the first guide element has a complementary shape to the shape of the rail of the second guide element.

6. The bone plug compression instrument according to claim 1, wherein the bone plug compression instrument comprises a toggle clamp mechanism for moving the second compression element.

7. The bone plug compression instrument according to claim 6, wherein the toggle clamp mechanism defines a dead centre position such that the closed configuration is reached from the open configuration by the toggle clamp mechanism exceeding the dead centre position for providing an increased compression force and self-restriction thereby inhibiting unwanted opening of the bone plug compression instrument.

8. The bone plug compression instrument according to claim 1, wherein:

the bone plug compression instrument comprises:

a second lever arm pivotably connected to the first lever arm by a second connection mechanism and to the base portion by a third connection mechanism such that:

when the first and second lever arms are in an elevated position with respect to the base portion, the bone plug compression instrument is in the open configuration, and when the first and second lever arms are in an opposite, non-elevated position with respect to the base portion, the bone plug compression instrument is in the closed configuration.

9. The bone plug compression instrument according to claim 8, wherein at least one of the first, second and third connection mechanisms is a hinge mechanism.

10. The bone plug compression instrument according to claim 1, wherein:

the first lever arm has a first end and a second, opposite end, the first end being pivotably connected to the second compression element by a first connection mechanism, and the second end comprises a contact surface configured to slide on a guiding surface of the base portion in order to move the second compression element between the first and second positions.

11. The bone plug compression instrument according to claim 10, wherein the contact surface is arranged in a guiding slot at least partially delimited by the guiding surface.

12. The bone plug compression instrument according to claim 1, wherein:

at least one of the first and second compression elements comprises a drilling channel sized and shaped to receive a drill bit, and the drill channel extends into the combined cavity and is directed towards a combined cavity central axis.

13. The bone plug compression instrument according to claim 1, wherein at least one of the first and second cavities comprises at least one spike for fixing the bone plug in the combined cavity during compression.

14. The bone plug compression instrument according to claim 1, wherein at least one of the first and second cavities has a length between 15 mm and 25 mm.

15. The bone plug compression instrument according to claim 1, wherein the combined cavity has a maximal inner circumference of at most 38 mm.

16. The bone plug compression instrument according to claim 1, wherein the combined cavity defines a tapering angle at its end, which is between 5° and 60°.

17. A kit comprising:

the bone plug compression instrument according to claim 1;

a bone grafting instrument for removing the bone plug from a target bone, the bone grafting instrument including:

a bore having a minimal bore inner circumference, and a cutting edge arranged circumferentially around the bore at a cutting end of the grafting instrument, wherein the combined cavity has a minimal combined cavity circumference, and the minimal combined cavity circumference is smaller than the minimal bore inner circumference.

18. A method of operating the bone plug compression instrument according to claim 1, the method comprising:

retrieving the bone plug using a bone grafting instrument;

inserting the bone plug in a substantially non-compressed state in the space between the first and second compression surfaces;

moving the second compression element from the first position to the second position so that the bone plug compression instrument reaches the closed configuration thereby reshaping the bone plug;

moving the second compression element from the second position to the first position so that the bone plug compression instrument reaches the open configuration; and removing the reshaped bone plug out of the bone plug compression instrument.

* * * * *